United States Patent [19]

Masaki et al.

[11] Patent Number: 4,987,123
[45] Date of Patent: Jan. 22, 1991

[54] COMPOSITIONS USEFUL FOR THE TREATMENT AND/OR PREVENTION OF HEPATIC DISORDERS, AND THEIR PHARMACEUTICAL USE

[75] Inventors: Hisanori Masaki; Kunio Torii, both of Kawasaki; Tomio Suda, Tachidawa, all of Japan

[73] Assignee: Ajinomoto Co., Inc., Tokyo, Japan

[21] Appl. No.: 243,610

[22] Filed: Sep. 13, 1988

Related U.S. Application Data

[63] Continuation-in-part of Ser. No. 161,139, Feb. 26, 1988, abandoned.

[30] Foreign Application Priority Data

Feb. 24, 1988 [JP] Japan ................................ 63-41368

[51] Int. Cl.$^5$ .................... A61K 37/02; A61K 31/195
[52] U.S. Cl. ...................................... 514/19; 514/561; 514/811
[58] Field of Search ................... 514/19, 561, 811

[56] References Cited

U.S. PATENT DOCUMENTS

| 4,258,037 | 3/1981 | Juvin ..................................... 514/561 |
| 4,596,825 | 6/1986 | Suda et al. ........................... 514/811 |
| 4,870,056 | 9/1989 | Nagasawa et al. ................... 514/811 |

FOREIGN PATENT DOCUMENTS 762M 8/1960 France ................................ 514/561

OTHER PUBLICATIONS

J. E. F. Reynolds: "Martindale, The Extra Pharmacopoeia", 28th Ed., 1982, The Pharmaceutical Press, London, GB; p. 48, Ref. No. 572-b: Alaine.

Dr. O.-A. Neumuller: "Rompps Chemic-Lexikon", 8th Ed., vol. 2: Cm-G, 1981, Franckh'sche Verlags-Handlung, Stuttgart, DE; p. 1509, . . .

Primary Examiner—Lester L. Lee
Attorney, Agent, or Firm—Oblon, Spivak, McClelland, Maier & Neustadt

[57] ABSTRACT

A composition, comprising L-alanine or a salt thereof, L-glutamine or a salt thereof, and an oligopeptide containing either a L-alanine residue or a L-glutamine residue, or both, is disclosed. A composition made up of (i) L-alanine or a salt thereof, (ii) L-glutamine or a salt thereof, and (iii) an oligopeptide containing a L-alanine or a L-glutamine residue is also discloed. The L-alanine and the L-glutamine are present in these compositions in an available molar ratio of from 1:0.1 to 1:10, respectively. These compositions are useful in the therapy or prevention of hepatic disorders.

17 Claims, 6 Drawing Sheets

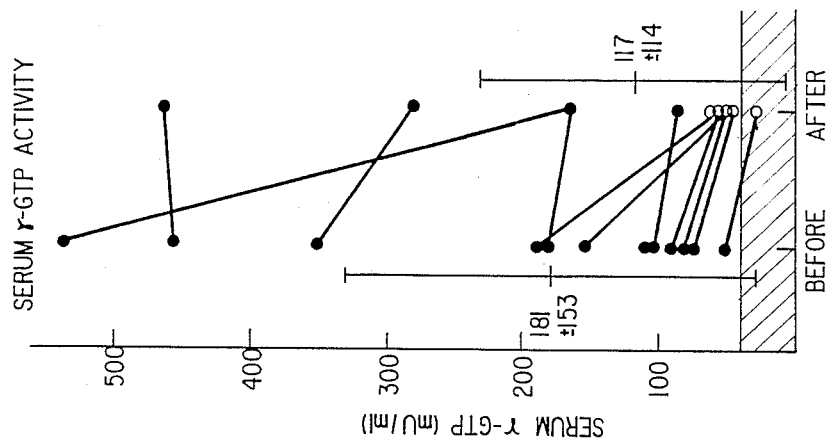
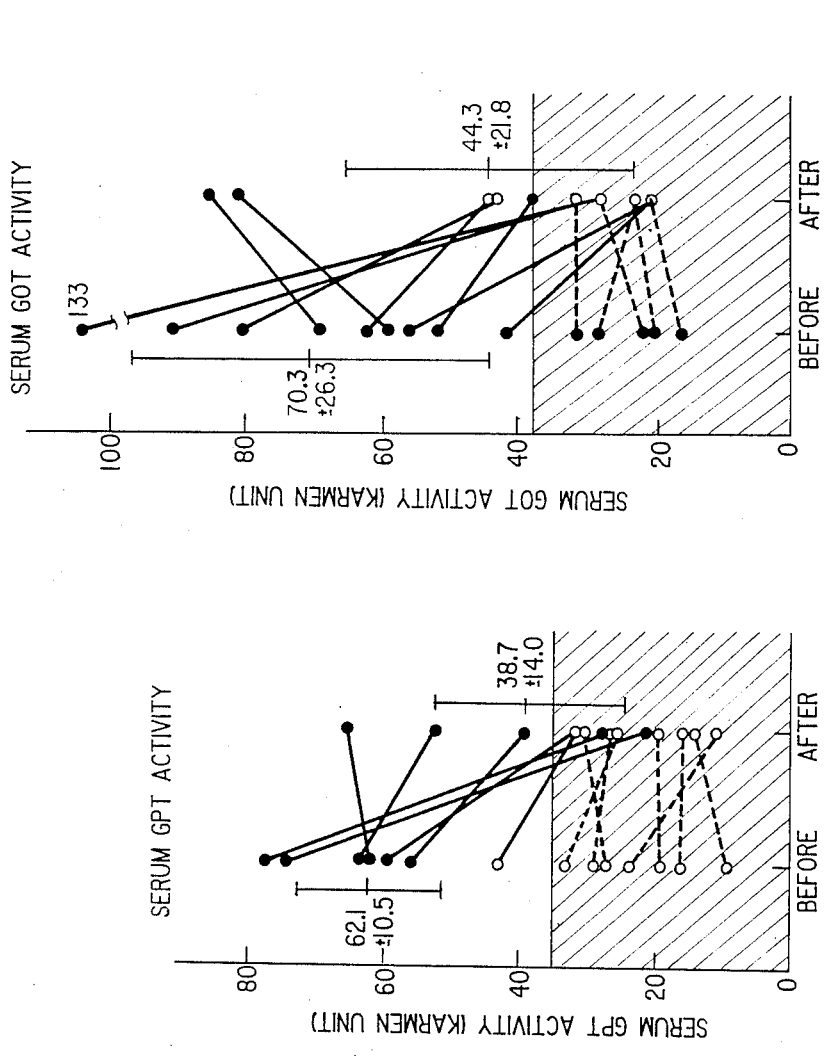
FIG. 8A
FIG. 8B
FIG. 8C

COMPOSITIONS USEFUL FOR THE TREATMENT AND/OR PREVENTION OF HEPATIC DISORDERS, AND THEIR PHARMACEUTICAL USE

This application is a continuation-in-part application of copending application Ser. No. 07/161,139, filed Feb. 26, 1988, now abandoned.

BACKGROUND OF THE INVENTION

1. Field of the Invention:

This invention relates to drugs and foods useful in the therapy of patients suffering from alcoholic hepatic disorders as well as its prevention.

2. Discussion of the Background:

The excessive ingestion of alcoholic (ethanolic) beverages chronically elicits various diseases, especially hepatic disorders and dysfunctions, such as fatty liver, alcoholic hepatitis, cirrhosis and so on. The liver is attacked because ethanol is catabolized specifically in this organ.

Total abstinence from alcoholic beverages is strongly recommended to patients with alcoholic hepatic disorders. These patients also receive therapy with drugs containing vitamins, phospholipids, glucocorticoids or insulin. In addition, drugs containing glucuronate or an amino acid, for example, L-arginine hydrochloride, are available to treat these patients.

Nonetheless, these treatments and prescriptions often fail to provide a complete regression of the disease. This is at least in part due to the fact that the patients still indulge in an occasional drink despite strongly recommended total abstinence.

Recently, it has become clear that some amino acids, for example, Ala etc., are quite potent at enhancing the survival rate of mice who have received a lethal dose of ethanol. In particular, concurrent treatment with Ala and L-ornithine has been reported to be synergistically effective (Petition for Japanese patent, Showa No. 61-50917).

It can also be recognized that rats display a preference for Ala as well as for Gln under dietary ethanol loading for periods of time (6 months or more), and that pretreatment of rats with both compounds ameliorated either ethanol clearance from the blood or recovery from a comatose state and the subsequent depression behavior which follows the ethanol loading. But these facts cannot be extrapolated to determine if a therapy of Ala and Gln for a progressed state of alcoholic hepatic disorders is effective or not.

It is known that the dizziness experienced after drinking is closely related to the concentration of acetoaldehyde in the drinker's blood. The concentration of this metabolite of ethanol in the blood is substantially elevated after drinking. Pretreatment with Ala, L-glutamate or aspartate decreases the toxicity of acetoaldehyde as a catabolite of ethanol, but does not suppress serum enzymatic activities, which are released from a damaged liver by ethanol loading, has ever occurred (Petition of Japanese patent, Showa No. 61-134313).

Therapy for patients suffering from alcoholic hepatic disorders induced by the excessive ingestion of ethanolic beverages has usually focused on attempts to ameliorate the degree of hepatic damage, mainly the parenchymal cell. However a complete regression is difficult for patients when the condition of the liver becomes worse and chronic. In addition, it is very hard to normalize serum enzymatic activity which is elevated by alcoholic hepatic damage because patients still indulge in drinking. Drugs for the hepatic damage and its prevention have been sought.

In view of the fact that the excessive consumption of alcoholic beverages is a widespread international phenomenon, there is a strongly felt need for a composition useful for therapy in the treatment of hepatic disorders and/or its prevention.

SUMMARY OF THE INVENTION

Accordingly, it is an object of this invention to provide a composition which is useful in the therapy of hepatic disorders.

It is another object of this invention to provide a composition which is useful in the prevention of hepatic disorders.

It is another object of this invention to provide a composition useful in therapy for alcoholic hepatic disorders.

It is another object of this invention to provide a composition useful for the prevention of alcoholic hepatic disorders.

It is another object of this invention to provide a foodstuff useful in the prevention of hepatic disorders.

It is another object of this invention to provide a foodstuff useful in the prevention of hepatic dysfunction.

It is another object of this invention to provide a foodstuff useful in the therapy of a hepatic disorder.

It is another object of this invention to provide a foodstuff useful in the therapy of alcoholic hepatic disorders.

It is another object of this invention to provide a method for the therapy of hepatic disorders.

It is another object of this invention to provide a method for the therapy of alcoholic hepatic disorders.

It is another object of this invention to provide a method for the prevention of hepatic disorders.

It is another object of this invention to provide a method for the prevention of alcoholic hepatic disorders.

The inventors have now discovered a composition which satisfies all of the above objects of this invention, and other objects which will become apparent from the description of the invention given hereinbelow. This composition comprises L-alanine (Ala) and L-glutamine (Gln). These two materials are present in a molar ratio of L-alanine to L-glutamine of from 1:0.1 to 1:10.

The present invention also provides a second composition comprising (i) L-alanine and/or a salt thereof, (ii) L-glutamine and/or a salt thereof, and (iii) a dipeptide and/or a salt thereof, containing either a L-alanine residue, a L-glutamine residue, or both. The L-alanine and L-glutamine are present in the composition in an available molar ratio of L-alanine to L-glutamine of from 1:0.1 to 1:10. The term "available" refers in this text to the amount of L-alanine and L-glutamine available to a patient upon administration of the composition to said patient.

The present invention also provides a composition in which the L-alanine component and the L-glutamine component are both present in the composition as components of the dipeptide.

This composition can be incorporated in a foodstuff or in a pharmaceutical composition. Thus the present invention also provides a foodstuff or a pharmaceutical composition containing an amount of L-alanine and L-glutamine in a molar ratio of from 1:0.1 to 1:10 effective for the treatment or prevention of a hepatic disorder or dysfunction.

The present invention also provides a composition containing both L-alanine and L-glutamine as the major component.

The present invention also provides a method for preventing a hepatic disorder, e.g., an alcoholic hepatic disorder. In this method, a patient is administered from 1 g to 20 g total of L-alanine and L-glutamine. The L-alanine and the L-glutamine being administered either individually or together in a molar ratio of from 1:0.1 to 1:10.

The present invention also provides a method for the therapy of a hepatic disorder, e.g., an alcoholic hepatic disorder. In this method from 1 g to 20 g total of L-alanine and L-glutamine are administered to the patient. The L-alanine and L-glutamine are administered in a molar ratio of L-alanine to L-glutamine of from 1:0.1 to 1:10.

In both the method for preventing a hepatic disorder or in the method for the therapy of a hepatic disorder, any of the compositions disclosed in this application can be used.

The L-alanine and L-glutamine used in the present invention are present either in their free form or as any well known pharmaceutically acceptable salts, e.g., their hydrochloride salts, etc.

BRIEF DESCRIPTION OF THE FIGURES

A more complete appreciation of the invention and many of its attendant advantages will be readily obtained as soon as the same becomes better understood by reference to the following detailed description when considered in connection with the accompanying figures.

Controls were intubated with vehicle (0.3% CMC in saline). Mean values with a standard error from intact rats without any treatment were noted in each figure.

Figure 6:
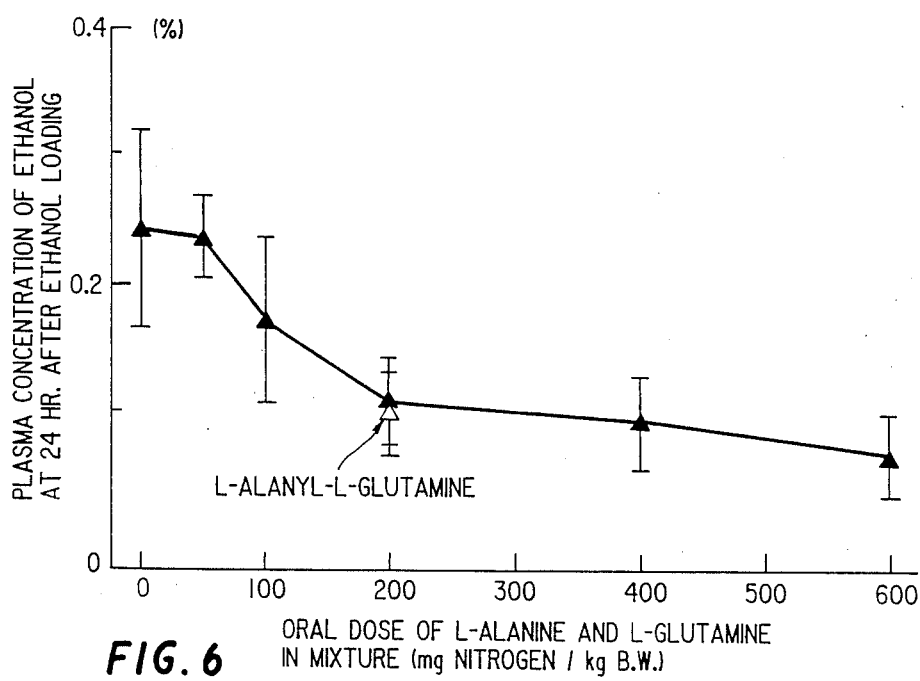

FIG. 6 provides the plasma concentration of ethanol at 24 hr after ethanol loading. Controls were intubated with vehicle (0.3% carboxymethyl cellulose in saline, abbreviated as CMC).

Figure 7A:
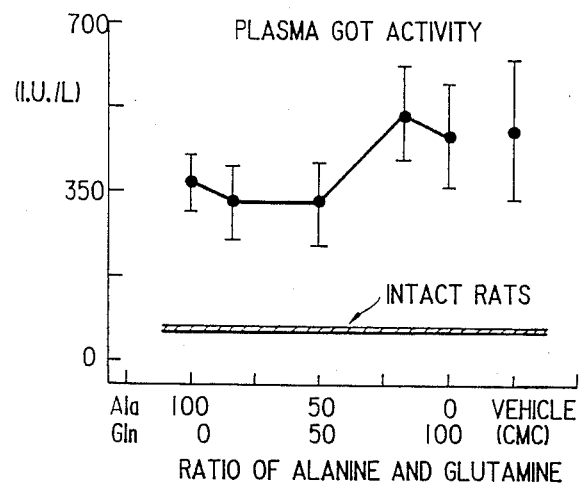
Figure 7B:
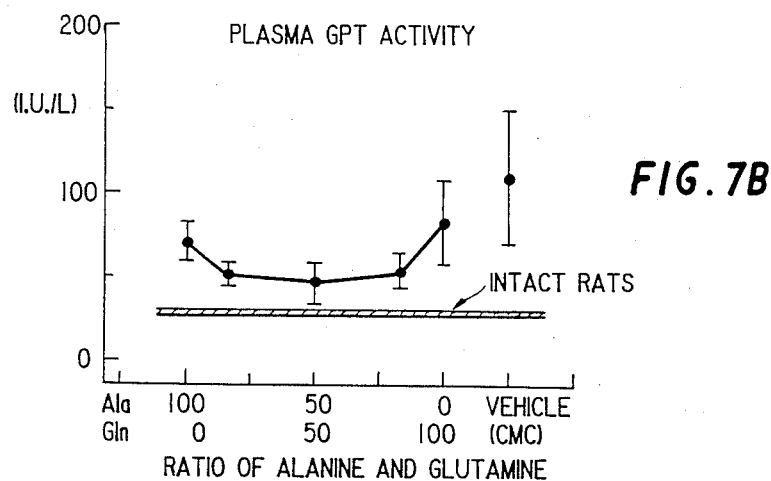
Figure 7C:
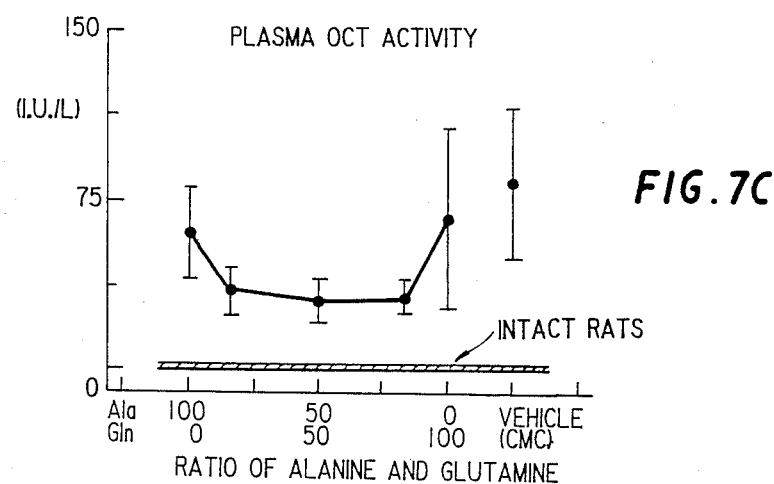

FIG. 7 provides enzymatic activity after ethanol loading:
(A) plasma GOT activity (upper);
(B) plasma GPT activity (middle); and
(C) plasma OCT activity (bottom).

Controls were intubated with vehicle (0.3% CMC in saline). Mean values with a standard error from intact rats without any treatment were noted with each figure.

FIG. 8 provides changes of enzymatic activity in the serum of patients with chronic alcoholic hepatitis and dysfunctions following therapy with L-alanine and L-glutamine orally.
(A) serum GPT activity (left);
(B) serum GOT activity (middle); and
(C) serum r-GPT activity (right).

The range of normal limits is noted in this figure by the shaded zone. The changes of enzymatic activity beyond the normal limit (●--------○) or within the normal limit (●--------○) are separately expressed in each figure. Data from patients with enzymatic activity beyond the normal limit before and after therapy with Ala and Gln are noted in each figure as the mean value with a standard error.

DETAILED DESCRIPTION OF THE PREFERRED EMBODIMENTS

The present invention provides a drug or a foodstuff useful in the treatment or prevention of hepatic disorders. The ingredients are L-alanine and L-glutamine. These two materials are present in a molar ratio of from 1:0.1 to 1:10, and are present in the composition in a form which makes them specifically available to the patient being treated.

The present invention thus provides a composition made up of (i) L-alanine and/or a salt thereof, (ii) L-glutamine and/or a salt thereof, and (iii) a dipeptide and/or a salt thereof, containing at least one L-alanine residue or at least one L-glutamine residue, or both. The amount of L-alanine and L-glutamine in this composition is that amount making a molar ratio of L-alanine to L-glutamine of from 1:0.1 to 1:10 available to a patient to which the composition is administered. Preferably, this ratio is 1:0.2 to 1:5. The dipeptide in this composition can be, for example, L-alanyl-L-glutamine or L-glutaminyl-L-alanine.

The present invention also provides a composition comprising as the major ($\geq 50$ wt. %) or as the only component containing either L-alanine or L-glutamine, an oligopeptide containing at least one L-alanine residue and at least one L-glutamine residue. The L-alanine and L-glutamine residues in this peptide are present in an amount sufficient to provide an available amount of L-alanine to L-glutamine of from 1:0.1 to 1:10, respectively, on a molar basis. Preferably this ratio is 1:0.2 to 1:5.

This dipeptide can be L-alanyl-L-glutamine or L-glutaminyl-L-alanine.

The present invention also provides a pharmaceutical composition containing an effective amount of the L-alanine and L-glutamine-containing compositions described above. The present invention also provides a foodstuff containing an effective amount of the L-alanine and L-glutamine-containing compositions described above.

The present invention further provides both a method for the therapy of an alcoholic hepatic disorder in a patient and a method for the prevention of an alcoholic hepatic disorder in a patient. In these methods an effective amount of one of the compositions of the present invention is administered to a patient in need thereof. The amount of administration of the composition is from 1 gram to 20 grams per day of the composition to the patient, where the patient weighs from 40 to 70 kilograms.

As will be seen from the discussion provided below, the present invention also relates to a composition containing as its main component L-alanine in a form suitable to make it available to a patient being subjected to therapy for a hepatic disorder or its prevention. The present invention also provides a composition containing L-glutamine as its main component, with the L-glutamine being present in the form which makes it available to a patient being subjected to a therapy for a hepatic disorder or its prevention.

The L-alanine and L-glutamine, whether used together or separately, can be present in any form as long as they are available to the patient. These forms include free L-alanine, free L-glutamine, their physiologically acceptable salts, or peptides which release L-alanine or L-glutamine, or both, in vivo.

These compositions contain an amount of L-alanine and L-glutamine sufficient to permit a total administration of from 1 g to 20 g of both of these materials to an adult being treated, on a per day basis. This dosage of 1 to 20 g a total of L-alanine and L-glutamine is administered to patients who weigh from 40 kg to 70 kg, with appropriate modifications of this dosage being possible for lighter and heavier patients.

The present invention also provides a foodstuff containing a mixture of L-alanine and L-glutamine as provided by this invention. Any well known foodstuff can be combined with this L-alanine and L-glutamine combination so long as a molar ratio of L-alanine to L-glutamine is from 1:0.1 to 1:10. This foodstuff can be used in the therapy of patients suffering from hepatic disorders, e.g. alcoholic hepatic disorders, or in prevention of these diseases.

The inventors have previously recognized that the plasma concentration of some L-amino acids, i.e., Ala and Gln declines with ethanol loading, and that this change could be suppressed by treatment of a patient with both of these compounds prior to ethanol loading. This pretreatment is also effective to ameliorate alcohol-specific syndromes including hypoglycemia, retention of ethanol in the blood, and the state of coma and depression behavior following excessive ingestion of alcoholic beverages. But there was not sufficient data from these observations for a determination of the effect of Ala and Gln on parameters associated with the degree of alcoholic hepatic disorders, such as serum enzymatic activities.

So the inventors tried to develop a new drug and the optimal ratio of Ala and Gln, on a molar basis, which should be administered orally to patients to combat these ethanol-specific syndromes. In these studies they used either (1) newly developed rat models for the acute hepatic damage by ethanol loading orally or (2) patients with chronic types of alcoholic hepatic disorders. The enzymatic activities in blood of rats and patients were monitored as parameters of the degree of the state of hepatic disorders.

The inventors determined from these studies that ethanol in blood is rapidly cleared and also that there was little possibility of eliciting histological changes in the liver similar to those of human alcoholic hepatitis when rats were receiving ethanol loadings at the nearly lethal dose as previously reported. Also, it has been attempted to establish chronic models for human hepatic disorders involving hepatitis induced by ethanol, but there are very rare reports using rats successfully to produce an adequate model to study the ethological mechanism in question.

The inventors therefore have tried to develop a new rat model for this disease, and have fortunately now found an acute model of alcoholic hepatitis in rats by treating them with ethanol loading with a small amount of hydrazine sulfate. In this model ethanol clearance from the blood is delayed, toxication is deteriorated, and serum enzymatic activities due to alcoholic hepatitis, such as glutamic oxaloacetic transaminase (GOT), glutamic pyruvic transaminase (GPT) and ornithine carbamyl transferase (OCT) is elevated.

The conditions simulated in this model became worse with dietary protein increase. This permitted a determination of the optimal molar ratio of Ala and Gln to cause (1) a beneficial effect on the promotion of ethanol clearance from the blood as well as (2) a suppression of serum enzymatic activities elevated by the elicitation of alcoholic hepatitis. This determination was made with rats pretreated with Ala and Gln in varied molar ratios prior to ethanol loading with hydrazine sulfate.

This invention provides conclusive evidence that a composition containing Ala and Gln in a molar ratio of from 1:0.1 to 1:10, preferably 1:0.2 to 1:5, provides a therapy for hepatic disorders when administered to a patient. This therapy includes treatment of alcoholic hepatic damage and its prevention.

The Ala and Gln used should be the L-form enantiomer as natural products. Of course, no troublesome side effects occur whenever the composition contains other isomers, i.e., any of the L-, D- and L- or D-form of both amino acids.

The Ala and Gln used can be in their free form, as any of various known physiologically acceptable salts, e.g. their hydrochloride salts, etc., or in a peptide which releases either of these, or both, in vivo. This composition is formulated with Ala and Gln in free form in any well known manner which can provide a total of from 1 g to 20 g of the active composition (Ala+Gln) per adult weighing from 40 kg to 70 kg per day. This amount can of course be adjusted for heavier or lighter adults.

It is effective and beneficial for Ala and Gln to be administered in the above described molar ratios. Therefore, it is also possible for each compound to be separately prepared and for both to be concurrently ingested.

Treatment of a patient with a composition containing Gln alone, or as the major component in a mixture, was observed to promote ethanol clearance from patients' blood and diminish depression, as well as death, after ethanol loading. On the other hand, treatment with a composition containing Ala alone, or dominantly, is quite effective in suppressing the elevation of serum enzymatic activities in rats after the elicitation of hepatitis by ethanol loading.

These data manifest the therapeutic effectiveness which occured in rats with an alcoholic hepatic disorder, when a composition was formulated with Ala and Gln in a molar ratio, measured with the compounds in their free forms, ranging from 1:1.01 to 1:10. The optimal ratio of these two compounds is about 1:1.

In addition, when 3 g of a composition containing Ala and Gln (in a molar ratio of 1:1.13), was administered to patients with chronic alcoholic hepatic disorders, their serum enzymatic activity, GOT, GPT and r-GTP, clearly declined, supporting the data from the experimental models mentioned above precisely. As a drug useful to decrease serum r-GTP activity, the composition provided by this invention is accordingly quite valuable in the therapy for this disease. The effective dosage of this composition and the sufficient duration for therapy in patients is recommended at not less than 1 g and up to 20 g of L-Ala and L-Gln total per adult per day, for a length of time of not less than one month. This administration can be maintained as long as necessary, e.g., years and up to the rest of the patient's life. Of course, the dosage and the duration can be adapted depending on the state of the disease.

In addition to Ala and Gln as free compounds, their salts or analogues, the present invention also contemplates compositions containing any peptides or proteins or any other compounds which are metabolized to free Ala and Gln in a living body. Such peptides, proteins or other compounds are known.

The composition provided by this invention is useful as a drug as well as a foodstuff so long as the limits of molar ratio and dosage described above are adhered to. It is recommended to use this ingredient as a pharmaceutical as follows: powdered, granulated, tablet-made, sugar-coated, capsule-mounted or a liquid drug. Additionally, beverages and chewing gums containing Ala and Gln are beneficially served to people concurrently or pre- and post-ingestion with alcoholic beverages and liquors.

Indeed, there is no trouble to formulate the present Ala and Gln composition concomitantly with other amino acids and/or their analogues as long as sufficient amounts and adequate molar ratios of Ala and Gln, the indispensable compounds, are present.

Other features of this invention will become apparent during the course of the following descriptions of exemplary embodiments which are given for illustration of the invention and are not intended to be limiting thereof.

EXAMPLE 1

Sprague-Dawley strain male rats, having 13 weeks of age and a body weight of around 120 g, where fed ad libitum a diet containing 14% (w/w) cyclodextrin included with 30% (w/w) ethanol for 200 days (N=6). Half the number of animals displayed body weight loss and alopecia 60 days after the experimental diet had been offered. The animals with an abnormal shape (the alopecia group) and the apparently normal ones (normal groups) were separated two groups (N=3, each group). Both groups of animals were supplied with 12 kinds of L-amino acids in distilled water and a vehicle.

The rats of the normal group displayed a strong preference for Ala and Gln in solution. But the rats of the alopecia group displayed a strong preference for Gln alone. They lost their body weight, and some of these rats died.

The rats of the alopecia group then began to prefer Ala, as was the case with the normal group, and subsequently, they recovered from alopecia and their body weight loss. The preference for Ala and Gln was sustained constantly until day=140 when the experiment was terminated. The molar ratio of Ala:Gln was as around 5:1.

EXAMPLE II

Sprague-Dawley strain rats, 10 weeks of age, were delivered on the same day to an animal room. Littermates were separated evenly into 5 groups (N=8). The rats in each group of animals (N=4, in a case) were housed in the large cage (35×37.5×35 cm) equipped with a titanium-made running wheel (100 cm per rotation) for 9 weeks until either the daily running distance or the diurnal pattern became constant. The animals were then used in this experiment.

Each animal was introduced to a restricted powdered diet (commerical laboratory chow) overnight (approximately 12–13 hr), and subsequently they were exposed to this diet for 2 hr. One hr. later, each group of animals was intubated with 0.7% (w/v) carboxymethyl cellulose (CMC) solution containing Ala and Gln (molar ratio of 5:1), Ala and Orn (molar ratio of 5:1) or an N-amino acid mixture (see Table 2).

The dosage of each experimental group, which was as much as the mean daily ingestion of both Ala and Gln described in Example 1, was isonitrogenous to each other (602 mg nitrogen/kg BW). The rest of the two groups were treated with vehicle (0.7% CMC solution as controls) in the same fashion.

Then three experimental groups and one control group (N=8 in each group) were injected with 10% (w/v) ethanol in saline (4.2 g/kg BW) intraperitoneally and the rest of one group did not receive ethanol but was kept as an intact control. Blood samples were collected from the infraclavicular vein 14 hr. after the ethanol loading and the plasma obtained was assayed for ethanol and glucose by the Bucher and Redetzki method (*Klin. Wochenschr* 29: 615, 1951), and Cawley (*Am. J. Clin. Pathol.* 29: 111, 1959), respectively.

In parallel, the running distance of each group was monitored using a microcomputer system and a photo encoder installed in the axle of the running wheel. Data for each group was compared to estimate the behavior depression due to ethanol loading. The plasma concentration of ethanol declined constantly as a function of time after ethanol treatment, and its clearance from the blood was more rapid in groups, Ala and Gln, Ala and Orn, and L-amino acid mixture, in order (Table 3). The plasma concentration of glucose in the control group dropped remarkably rather than that in the intact control group. This level in groups, Ala and Gln, as well as Ala and Orn, still remained near to that in the intact control group, but the pretreatment with the L-amino acid mixture did not have an effect (Table 3).

In addition, the severe behavior depression in each group induced by ethanol toxication, which degrees of suppression ranged from 92% to 97% of value in the intact control group, were observed all day long after the treatment. On the following day, this depression became weaker and mostly normal, in groups among Ala and Gln, Ala and Orn, and L-amino acid rather than that in the control group (Table 4).

EXAMPLE III

Sprague-Dawley strain male rats, 10 weeks of age and having a body weight of around 300 g were used. Each animal was housed in a stainless steel-made cage individually and fed a commercial laboratory chow ad libitum until 3 days prior to treatment. The animal room was illuminated from 7 a.m. for 12 hr. An experimental diet containing 15% (w/w) whole egg protein (PEP) was offered to the rats for 2 days, then a high protein diet with 50% PEP was offered for 2 days. On the first day of the high protein diet being offered, each animal was intubated with Ala and/or Gln, in suspension with 0.3% carboxymethyl cellulose (201 mg Nitrogen/kg BW) or vehicle (control), as a pretreatment (N=10, each group). The ratio of both compounds in the mixture was varied as follows: Ala or Gln alone, and both Ala and Gln in molar ratio as 1:0.2, 1:1, or 1:5.

The rats were intubated again with 20% (w/v) ethanol in saline (6 g/kg BW) with 0.13% (w/v) hydrazine sulfate (0.3 mmole/kg BW) 1 hr after the pretreatment. Blood sample collections from the infraclavicular vein of individuals in each group including control were made at 3 and 24 hr after the treatment. Clinical observations were also carried at 3 and 20 hr. after treatment. The concentration of ethanol in plasma was assayed by the Bucher and Redetzki method (*Klin. Wochenschr* 29: 615, 1951). The comatose state in individuals after the ethanol loading orally were scored as follows: 0=dead or moribund, 1=comatose, 2=dizzy, and 3=conscious. Data from present study were expressed as mean value with a standard error and summarized in FIGS. 1 and 2.

Figure 1:
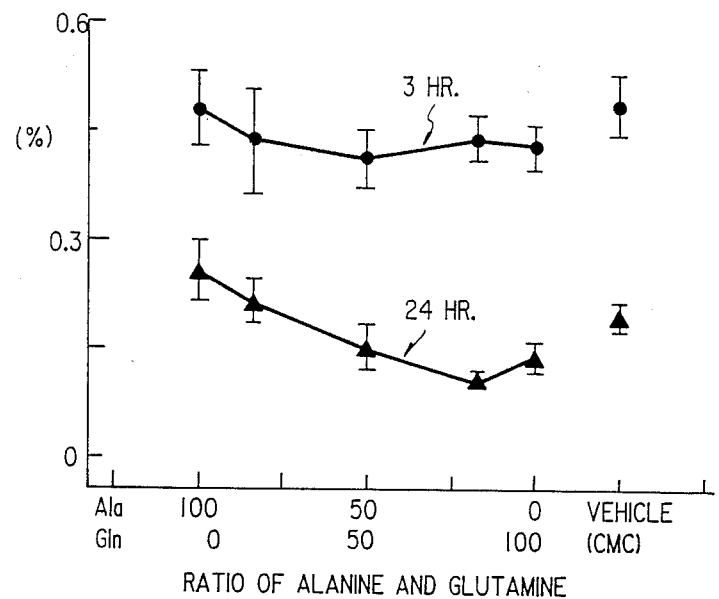
FIG. 1 provides plasma concentrations of ethanol: (a) three hours after ethanol loading (upper); (b) 24 hours after ethanol loading (bottom). Controls were intubated with vehicle (0.3% of carboxymethyl cellulose in saline, abbreviated as CMC).
Figure 2:
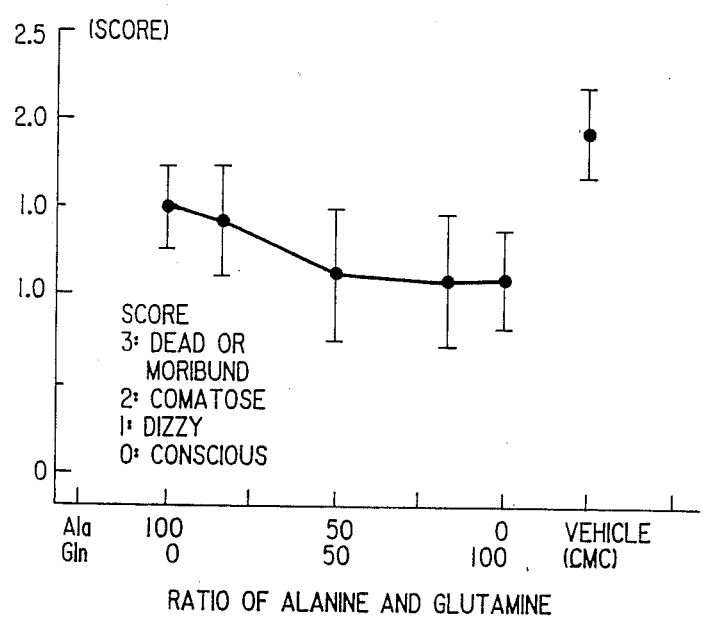
FIG. 2 provides recovery from the comatose state 20 hours after ethanol loading. The degree of recovery from the comatose state in each rat tested was scored as follows: (3)=dead or moribund; (2)=still comatose; (1)=dizzy and depressed; and (0)=conscious and completely recovered. Controls were intubated with vehicle (0.3% CMC in saline).

The concentration of ethanol in plasma of the group receiving Gln alone after 3 hr. of ethanol loading orally, was lowered significantly in comparison with controls. This effect was much more enhanced in any groups receiving mixture of Ala and Gln, which molar ratio in molar was not less than the value 1:1. This characteristic change became clearer at 24 hr after ethanol treatment (FIG. 1). On the other hand, the comatose state in each group was essentially the same at 3 hr. after ethanol loading, but the recovery from this coma at 20 hr. following treatment was greatly ameliorated by the intubation of both Ala and Gln as a pretreatment. This effect was enhanced as the Gln moiety was increased in the mixture, and reached a plateau level when the molar ratio (Ala:Gln) was not less than the value 1:1 (FIG. 2).

EXAMPLE IV

Sprague-Dawley strain male rats, 10 weeks of age and having a body weight of around 300 g were used. Each animal was housed in a stainless steel-made cage individually and fed a commercial laboratory chow ad libitum until 3 days prior to treatment. The animal room was illuminated from 7 a.m. for 12 hr. An experimental diet containing 15% (w/w) PEP was offered to rats for 2 days, then a high protein diet with 50% PEP for 2 days. On the first day of the high protein diet being offered, each animal was intubated with Ala and/or Gln in suspension with 0.3% carboxymethyl cellulose (201 mg Nitrogen/kg BW) or vehicle (control) as a pretreatment. The ratio of both compounds in the mixture was varied as follows: Ala or Gln alone, and both Ala and Gln in molar as 1:0.2, 1:1, or 1:5 (N=5, each group).

The rats were intubated again with 20% (w/v) ethanol in saline (7 g/kg BW) with 0.11% (w/v) hydrazine sulfate (0.3 mmole/kg BW) 1 hr. after the pretreatment. A clinical observation of individuals in each group including controls was made at 3, 24 and 72 hr. after the ethanol treatment.

Figure 3A:
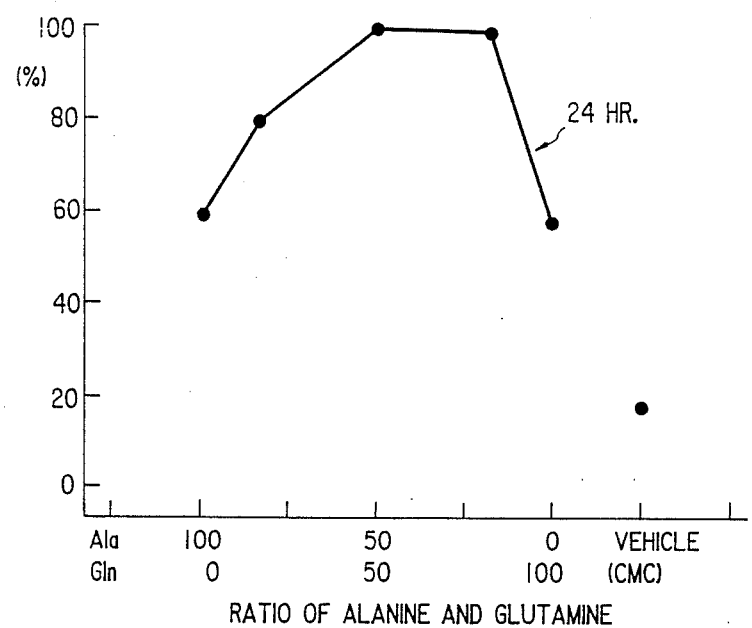
FIG. 3 provides the survival rate after ethanol loading: (a) 24 hours after treatment (upper); (b) 72 hours after treatment (bottom). Controls were intubated with vehicle (0.3% CMC in saline).
Figure 3B:
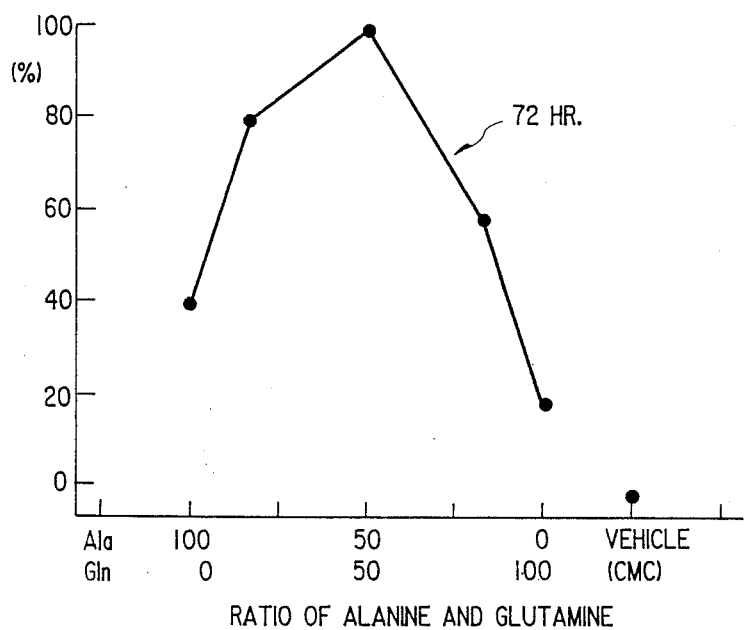

The survival rate of each group was recorded and summarized in FIG. 3. Only one rat in five controls, having received the intubation of vehicle as a pretreatment, was alive at 24 hr. and all the animals had died at 72 hr. after ethanol loading. But the survival rate of any group having received the intubation of Ala and/or Gln, was beyond that in controls. The results were as follows: Ala alone, 3/5; Gln alone, 4/5; and both at molar ratios of Ala:Gln of 1:0.2=1/5; at 1:1=0/5 and at 1:5=2/5.

EXAMPLE V

Sprague-Dawley strain male rats, 16 weeks of age, and having a body weight ranging around 450 g, were used. Each animal was housed in a stainless steel-made cage individually and fed a commercial laboratory chow ad libitum until 3 days prior to treatment. The animal room was illuminated starting at 7 a.m. for 12 hr. An experimental diet containing 15% (w/w) PEP was offered to the rats for 2 days, then a high protein diet with 50% PEP for 2 days. On the first day of high protein diet offered, each animal was intubated with Ala and Gln (molar ratio as 1:1) in suspension with 0.3% (w/v) carboxymethyl cellulose at doses of 50, 100, 200, 400 and 600 mg Nitrogen/kg BW or vehicle (control) as a pretreatment (N=7, each group).

Figure 4:
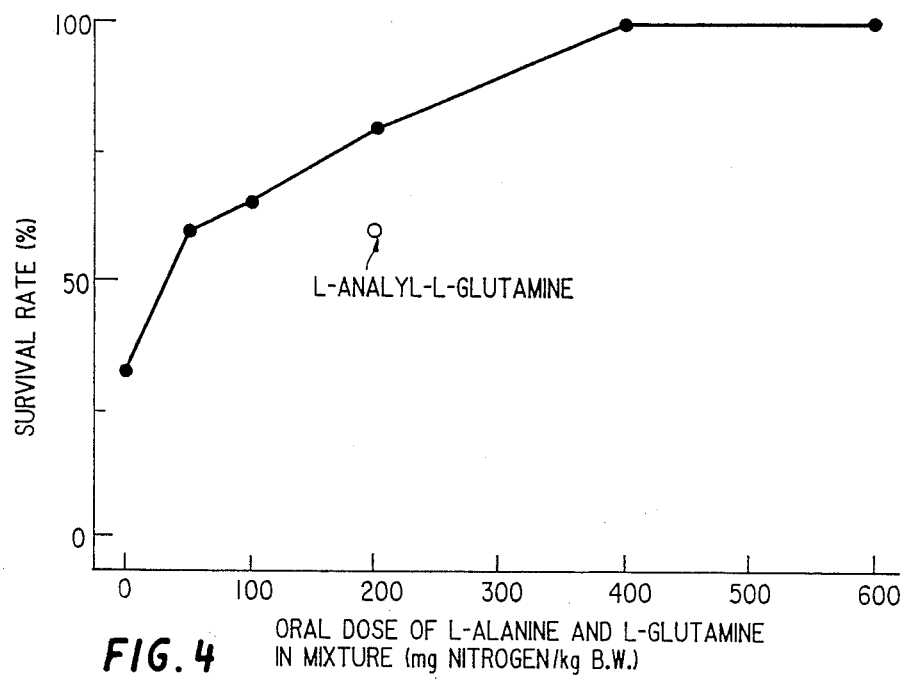
FIG. 4 provides the survivor rate at 24 hr after ethanol loading. Controls were intubated with vehicle (0.3% CMC in saline).
Figure 5A:
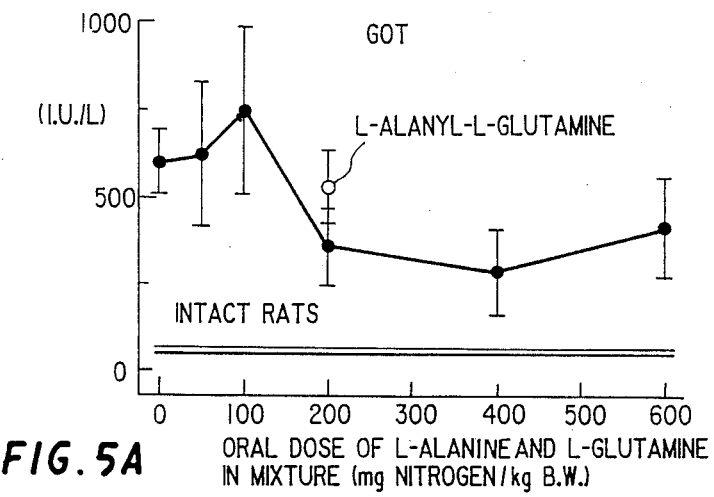
FIG. 5 provides the enzymatic activities after ethanol loading:
(A) Plasma GOT activity (upper);
(B) Plasma GPT activity (middle); and
(C) Plasma OCT activity (bottom).
Figure 5B:
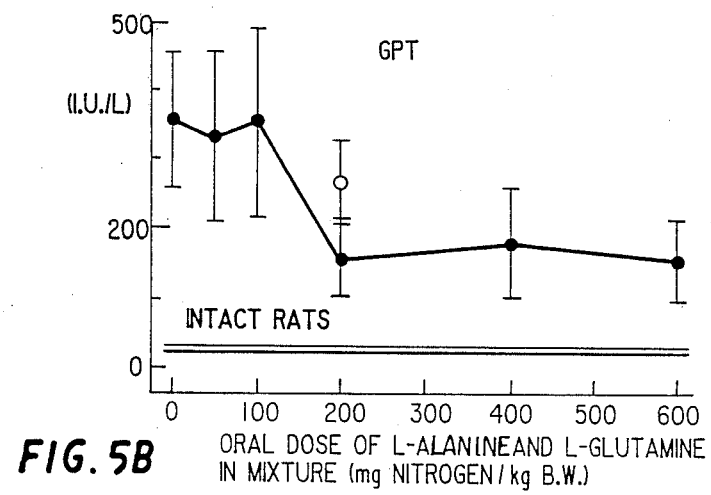
Figure 5C:
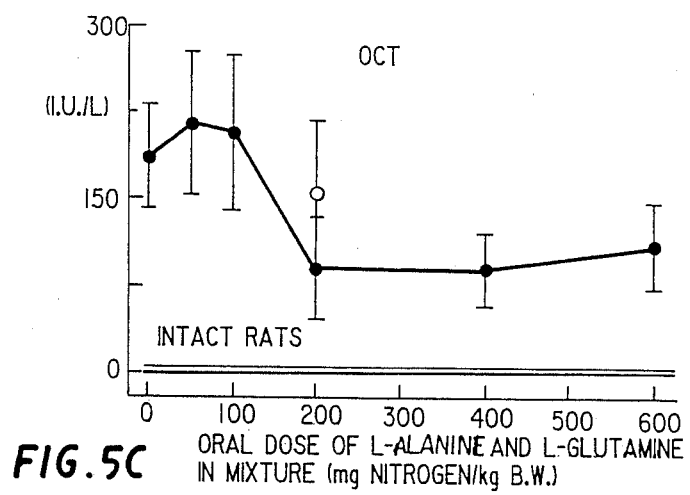

They were intubated again with 20% (w/v) ethanol in saline (5 or 6 g/kg VW) with 0.13% (w/v) hydrazine sulfate (0.3 mmole/kg BW) 1 hr after the pretreatment. Either blood collection from the infraclavicular vein of survivors or the clinical observation of individuals at 3 and 24 hr after the treatment was carried out. The yielded plasma was assayed for enzymatic activities being derived specifically from the liver following alcoholic hepatitis induced by the ethanol loading orally; GOT and GPT by the method of Karmen (*Am. J. Clin. Path.* 34:381, 1960) and OCT by the method of Takeda (*Clin. Chim. Acta.* 67:145, 1976). The survivor rate of each experimental group which received higher ethanol loading (6 g/kg BW) is summarized in FIG. 4, but no animals died which had received the lower dose of ethanol (5 g/kg BW). These enzymatic activities and the ethanol in the plasma of each group of rats after ethanol loading (5 g/kg BW) were severely suppressed as the dosage of Ala and Gln increased (FIG. 5). In addition, pretreatment with L-alanyl-L-glutamine also suppressed these activities despite a lower degree in comparison with the equivalent dosage of Ala and Gln. Furthermore, the ethanol clearance from the blood after ethanol loading (5 g/kg BW) was comparable to the case of rats which received an equivalent dosage of Ala and Gln (FIG. 6).

These effects suggested that L-alanyl-L-glutamine is potent in ameliorating hepatitis, including acute alcoholic hepatitis.

EXAMPLE VI

Sprague-Dawley strain male rats, 10 weeks of age and having a body weight of around 300 g were used. Each animal was housed in a stainless steel-made cage individually and fed a commercial laboratory chow ad libitum until 3 days prior to treatment. The animal room was illuminated from 7 a.m. for 12 hr. An experimental diet containing 15% (w/w) PEP was offered to rats for 2 days, then a high protein diet with 50% PEP for 2 days. On the first day of the high protein diet being offered, each animal was intubated with Ala and/or Gln in suspension with 0.3% (w/v) carboxymethyl cellulose (201 mg Nitrogen/kg BW), or vehicle (control) as a pretreatment (N=10, each group). The ratio of both compounds in the mixture was varied as follows: Ala or Gln alone, and both Ala and Gln in molar ratios of 1:0.2, 1:1, or 1:5.

The rats were intubated again with 20% (w/v) ethanol in saline (6 g/kg BW) with 0.13% (w/v) hydrazine sulfate (0.3 mmole/kg BW) 1 hr. after the pretreatment.

Either a blood collection from the infraclavicular vein or a clinical observation was made of individuals at 3 and 24 hr. after the treatment. The yielded plasma was assayed for enzymatic activities being derived specifically from the liver following the alcoholic hepatitis induced by the ethanol loading orally; GOT and GPT by the Karmen method (*Am. J. Clin. Path.* 34: 381, 1960) and OCT by the Takeda method (Clin. Chim. Acta. 67: 145, 1976). Data from each experimental group is summarized in FIG. 4 and mean values with a standard error of intact rats are noted in this figure. The enzymatic activities in plasma of controls were greatly enhanced by the ethanol loading, suggesting that acute hepatitis occurred. But any pretreatment of Ala and/or Gln clearly suppressed the increments of these activities, especially the combination of both compounds was found to be more effective rather than either compound alone (FIG. 7).

EXAMPLE VII

Fourteen patients with alcoholic hepatitis, which were free from hepatic virus, i.e., types A and B, were selected among people who had consumed large amounts of alcoholic beverages constantly for a long time (more than 20 years) and had been in consultation for their diseases with a hospital. They received a therapy of Ala and Gln in mixture orally (1 g) three times until 30 min. after a meal (total=3 g per day) for a prolonged period ranging from 1 to 6 months. The molar ratio of Ala and Gln was 1:0.12. The enzymatic activities among GOT, GPT or r-GTP in the serum of patients, having been beyond the normal limits, became lower than before the beginning of this therapy and data was noted as follows: GPT, 6 in 7 cases, 7 in 9, r-GTP, 13 in 14 (FIG. 8).

Neither complaints nor any adverse effect relating to this treatment were observed. Also there was no case in which the prescription and protocol of this therapy was not observed, but almost all the patients still consumed alcoholic beverages despite strong recommendations of abstinence from drinking. These data indicate that a therapy with Ala and Gln in mixture orally could be effective to ameliorate the state of alcoholic hepatitis.

From the evidence provided herein, it is clear that a mixture of Ala and Gln is particularly useful either as a clinical drug for the treatment of hepatic dysfunction, including alcoholic hepatitis, or to prevent this disease in people who have the habit of drinking a lot. This discovery is very valuable in its pharmaceutical applications.

Descriptions of Tables and Figures

The changes of preferences for L-amino acid in rats fed a diet containing 14% (w/w) ethanol including cyclodextrin were monitored and data were expressed as the mean value of daily intake in Table 1 (Example 1). The effect of L-amino acid pretreatment, including L-amino acid mixture (Table 2), on either the plasma concentration of ethanol and glucose at 14 hr. are shown in Table 3 or the running distance as a parameter of spontaneous motor activity in rats after ethanol loading orally in Table 4 were shown (Example II). The plasma concentration of ethanol and the comatose state in ethanol treated rats, intubated with Ala and/or Gln as a pretreatment (Example III) are shown in FIG. 1 and 2. The survival rate (Example IV) and the enzymatic activities in serum of rats (Example VI) are shown in FIGS. 3 and 7. The data obtained using L-alanyl-L-glutamine was similar to the data obtained using Ala and Gln (molar ratio=1:1) (Example V) (FIGS. 4, 5 and 6). In addition data for patients with alcoholic hepatitis (Example VII) is shown in FIG. 8.

Table 1. Daily intake of L-amino acid solution in rats fed a diet containing 14% (w/w) ethanol including cyclodextrin.

Each L-amino acid was dissolved in deionized water in the most preferable concentration. The experimental diet contained 4.2% (w/v) ethanol. The mean values of each solution intake were noted.

TABLE 1

| | Daily intake of L-amino acid solution (ml/rat/day) | | |
|---|---|---|---|
| | Group of rats | | |
| | Abnormal (alopecia) (day 10) | Normal (day 10) | Normal (day 140) |
| 200 mM L-Gln | 29 | 28 | 14 |
| 50 mM L-His | 0 | 0 | 0 |
| 35 mM L-Val | 0 | 0 | 0 |
| 50 mM L-Arg | 3 | 1 | 5 |
| 400 mM L-Thr | 0 | 1 | 3 |
| 45 mM L-Phe | 1 | 0 | 0 |
| 150 mM L-Glu.Na | 0 | 2 | 4 |
| 200 mM L-Ser | 2 | 0 | 1 |
| 400 mM L-Lys.HCl | 0 | 2 | 1 |
| 150 mM L-Met | 1 | 0 | 1 |
| 500 mM L-Ala | 0 | 32 | 29 |
| 500 mM Gly | 0 | 0 | 4 |

Table 2. Compostion of L-amino acid mixture.

The L-amino acid was milled by pulverizer and mixed together on the basis of weight per weight.

TABLE 2

| Composition of L-amino acid mixture | |
|---|---|
| | (%) |
| L-Ile | 4.5 |
| L-Leu | 6.4 |
| L-Lys.HCl | 6.3 |
| L-Met | 4.6 |
| L-Phe | 6.2 |
| L-Thr | 3.7 |
| L-Trp | 1.1 |
| L-Val | 5.0 |
| L-Ala | 6.4 |
| L-Arg.HCl | 8.0 |
| L-Asp.Na.H$_2$O | 6.2 |
| L-Asp.Mg | 7.3 |
| L-Gln | 13.7 |
| Gly | 3.6 |
| L-His.HCl.H$_2$O | 3.5 |
| L-Pro | 4.5 |
| L-Ser | 8.2 |
| L-Tyr | 0.8 |
| Total | 100.0 |

Table 3. Plasma concentration of ethanol and glucose 14 hr. after ethanol loading orally with or without the pretreatment of L-amino acid intubation. Both mean values in each group were summarized.

TABLE 3

| | Plasma concentration of ethanol and glucose 14 hours after ethanol loading | | | | |
|---|---|---|---|---|---|
| | Ala & Gln | Ala & Orn | Amino Acid mixture | Control | Intact Control |
| Ethanol (%) | 0.075 | 0.082 | 0.109 | 0.123 | — |
| Glucose (mg/dl) | 178 | 178 | 134 | 136 | 200 |

Table 4. Spontaneous motor activity in rats after ethanol loading with or without pretreatment with L-amino acid intubation.

The daily running distance as a parameter of spontaneous motor activity was monitored by a running wheel at Day 1 and Day 2 after ethanol loading. The mean value in each group was summarized by a microcomputer system using the photoencoder installed in the axle of the running wheel.

TABLE 4

| | Spontaneous motor activity monitored by running wheel after ethanol loading | | | | |
|---|---|---|---|---|---|
| | Ala & Gln | Ala & Orn | Amino Acid mixture | Control | Intact Control |
| Day 1 | 160 | 100 | 116 | 61 | 2133 |
| Day 2 | 1838 | 974 | 1004 | 501 | 2746 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A pharmaceutical composition, comprising L-alanine and L-glutamine, wherein said L-alanine and said L-glutamine are present in a molar ratio of from 1:0.1 to 1:10, respectively.

2. The composition of claim 1, wherein said ratio is 1:0.2 to 1:5, respectively.

3. A composition, comprising:
   (i) L-alanine in free form, a salt of L-alanine, and/or a peptide capable of releasing L-alanine in vivo; and
   (ii) L-glutamine in free form, a salt of L-glutamine and/or a peptide capable of releasing L-glutamine in free form;
   wherein (i) and (ii) are present in an amount such that, the molar ratio of L-alanine and L-glutamine available to a patient to which the composition has been administered is 1:0.1 to 1:10, respectively.

4. The composition of claim 3, wherein said peptide is L-alanyl-L-glutamine or L-glutaminyl-L-alanine.

5. A pharmaceutical composition, comprising a pharmaceutical excipient in association with a combination of L-alanine and/or a salt thereof and/or a peptide capable of releasing L-alanine in vivo, and L-glutamine and/or a salt thereof and/or a peptide capable of releasing L-glutamine in vivo, wherein said L-alanine and said L-glutamine are present in a molar ratio of from 1:0.1 to 1:10, respectively.

6. The pharmaceutical composition of claim 5, wherein said L-alanine and said L-glutamine are present in said pharmaceutical composition in an amount sufficient to permit a total administration to a patient of both L-alanine and L-glutamine of from 1 g to 20 g per day.

7. The pharmaceutical composition of claim 5, said composition being in a form suitable for oral administration.

8. In a foodstuff, the improvement comprising L-alanine, and/or a salt thereof, and/or a peptide capable of releasing L-alanine in vivo, and L-glutamine, and/or a salt thereof, and/or a peptide capable of releasing L-glutamine in vivo, wherein said L-alanine and said L-glutamine are present in a molar ratio of from 1:0.1 to 1:10, respectively.

9. The foodstuff of claim 8, wherein said foodstuff comprises a beverage or a chewing gum.

10. A method for the therapy of an alcoholic hepatic disorder in a patient, said method comprising administering to said patient from 1 g to 20 g per day of a composition containing L-alanine, a salt thereof, and/or a peptide capable of releasing L-alanine in vivo, and L-glutamine, a salt thereof, and/or a peptide capable of releasing L-glutamine in vivo, wherein said L-alanine and said L-glutamine are present in an amount available to said patient corresponding to a molar ratio of L-alanine to L-glutamine of from 1:0.1 to 1:10.

11. A method for the prevention of an alcoholic hepatic disorder in a patient, comprising administering to said patient from 1 g to 20 g per day of a composition containing L-alanine, a salt thereof, and/or a peptide capable of releasing L-alanine in vivo, and L-glutamine, a salt thereof, and/or a peptide capable of releasing L-glutamine in vivo, wherein said L-alanine and said L-glutamine are present in an amount available to patient corresponding to a molar ratio L-alanine to L-glutamine of from 1:0.1 to 1:10.

12. A pharmaceutical composition, comprising a pharmaceutically acceptable excipient and L-glutamine in an amount effective for the therapy or prevention of a hepatic disorder.

13. The method of claim 10, wherein the patient to whom from 1 g to 20 g per day of said composition are administered weighs from 40 to 70 kg.

14. The method of claim 11, wherein said patient to whom 1 g to 20 g of said composition are administered per day weighs from 40 to 70 kg.

15. The method of claim 10, comprising administering said composition to said patient for at least one month.

16. A pharmaceutical composition comprising a pharmaceutically acceptable excipient and a mixture of L-alanine and L-glutamine, in free or salt form, in an amount effective for the therapy or prevention of a hepatic disorder.

17. The pharmaceutical composition of claim 16 wherein the molar ratio of L-alanine to L-glutamine in the composition is 1:0.1 to 1:10 respectively.

* * * * *